United States Patent [19]
Abe et al.

[11] Patent Number: 5,312,966
[45] Date of Patent: May 17, 1994

[54] PROCESS FOR PRODUCTION OF CARBOXYLIC ACID ESTER AND FORMAMIDE

[75] Inventors: Takafumi Abe; Yoshiyuki Nishide; Nobuyuki Muro; Hirofumi Higuchi, all of Niigata, Japan

[73] Assignee: Mitsubishi Gas Chemical Company, Inc., Tokyo, Japan

[21] Appl. No.: 944,359

[22] Filed: Sep. 14, 1992

[30] Foreign Application Priority Data

Dec. 26, 1991 [JP] Japan .................... 3-345190

[51] Int. Cl.$^5$ .................... C07C 69/675; C07C 69/34; C07C 69/68; C07C 69/54
[52] U.S. Cl. .................... 560/179; 560/103; 560/155; 560/215; 560/265; 564/215
[58] Field of Search ............... 560/179, 215, 265, 103, 560/155; 564/215

[56] References Cited

U.S. PATENT DOCUMENTS

| | | | |
|---|---|---|---|
| 4,613,684 | 9/1986 | Aoyama et al. | 560/179 |
| 4,973,739 | 11/1990 | Nagasawa et al. | 560/179 |
| 4,983,757 | 1/1991 | Ishikawa et al. | 560/179 |
| 4,990,651 | 2/1991 | Ikarashi et al. | 560/179 |
| 5,087,736 | 2/1992 | Higuchi et al. | 560/215 |
| 5,087,737 | 2/1992 | Higuchi et al. | 560/215 |
| 5,194,668 | 3/1993 | Ikarashi et al. | 560/103 |

FOREIGN PATENT DOCUMENTS

| | | | |
|---|---|---|---|
| 0342458 | 11/1989 | European Pat. Off. | 560/179 |
| 0342475 | 11/1989 | European Pat. Off. | 560/179 |
| 0392361 | 10/1990 | European Pat. Off. | 560/179 |
| 0413140 | 2/1991 | European Pat. Off. | 560/179 |
| 53-14452 | 2/1978 | Japan . | |
| 53-141216 | 12/1978 | Japan . | |
| 58-55444 | 4/1983 | Japan . | |
| 60-78937 | 5/1985 | Japan . | |
| 2-255640 | 10/1990 | Japan . | |
| 2-268137 | 11/1990 | Japan . | |
| 3-48637 | 3/1991 | Japan . | |

*Primary Examiner*—Jose'G. Dees
*Assistant Examiner*—B. Frazier
*Attorney, Agent, or Firm*—Frishauf, Holtz, Goodman & Woodward

[57] ABSTRACT

There is disclosed a process for efficiently producing a carboxylic acid ester and formamide by reacting a carboxylic acid amide with a formic acid ester or with an alcohol and carbon monoxide in the presence of a strongly basic anion-exchange resin. By the use of the strongly basic anion-exchange resin as the catalyst, the process of the present invention enables the efficient production of the carboxylic acid ester as well as formamide from the Carboxylic acid amide and Formic acid ester, etc. with a high selectivity under mild reaction conditions and facilitates the separation of the catalyst from the reaction product, thereby greatly enhancing the industrial significance of itself.

20 Claims, No Drawings

PROCESS FOR PRODUCTION OF CARBOXYLIC ACID ESTER AND FORMAMIDE

BACKGROUND OF THE INVENTION

1. Field of the Invention

The present invention relates to a process for production of a carboxylic acid ester and formamide. More particularly it pertains to a process for efficiently producing a carboxylic acid ester and formamide from a carboxylic acid amide and formic acid ester or from a carboxylic acid amide, an alcohol and carbon monoxide (hereinafter referred to as "Carboxylic acid amide and Formic acid ester, etc." including the above two combinations).

2. Description of Related Art

Carboxylic acid esters are industrially important compounds. As the processes for producing a carboxylic acid ester from a carboxylic acid amide, there are available, for example, the process for production of methyl acetate from acetic acid amide, that of methyl methacrylate from methacrylic acid amide, that of methyl acrylate from acrylic acid amide, that of methyl α-hydroxyisobutyrate from α-hydroxyisobutyric acid amide.

Formamide is used as a solvent, a treating agent, an electrolyte, an antifreezing agent, a starting material for producing hydrogen cyanide or as an intermediate for production of a medicine, a dye, a pigment or for organic synthesis.

As the process for producing a carboxylic acid ester from a carboxylic acid amide, there has heretofore been known a process wherein a carboxylic acid amide is reacted with an alcohol in the presence of sulfuric acid, which process has been widely put into practice for the industrial production of methyl methacrylate. However, the aforesaid process is confronted with such problems as the production of a large amount of acidic ammonium sulfate, a high cost required for the disposal thereof and the necessity of expensive corrosion-resisting equipment.

As the process without the use of sulfuric acid, there is proposed, for example, in Japanese Patent Application Laid-Open Nos. 14452/1978, 141216/1978, etc. a process wherein a carboxylic acid ester is produced by the catalytic reaction of a carboxylic acid amide with an alcohol. The aforementioned process, however, involves various problems in industrial application such as the low yield and low selectivity of the objective carboxylic acid ester, the formation of a large amount of ammonia necessitating the separation and recovery thereof and the formation of an ammonium salt by the reaction with a by-produced carboxylic acid.

As the process without the formation of ammonia, there is disclosed in Japanese Patent Application Laid-Open Nos. 55444/1983 and 78937/1985 a process wherein a carboxylic acid amide is reacted with a formic acid ester instead of alcohol to produce the objective carboxylic acid ester and formamide. In the above process, however, it is necessary to separate or deactivate the catalyst immediately after the reaction as the reaction proceeds as an equilibrium reaction. In addition, the above process suffers the disadvantages that the catalyst system is expensive and requires complicated steps for the regeneration and recycling of the catalyst, since the catalyst is composed of a metal salt of an organic or inorganic acid or a metal chelate compound in combination with an organic compound containing nitrogen or phosphorus or of an amidine or tertiary amine combined with a metal carbonyl.

There is also proposed in Japanese Patent Application Laid-Open Nos. 255640/1990, 268137/1990 and 48637/1991 a process wherein a carboxylic acid amide is reacted with a formic acid ester to produce the object carboxylic acid ester and formamide by the use of a catalyst composed of a dehydration condensation product of an alkali metal alcoholate, an alkaline earth metal oxide or a carboxylic acid amide with an alkali metal hydroxide or an alkaline earth metal hydroxide. The above-mentioned catalyst is relatively inexpensive and does not necessarily require recycling of itself, but still involves the problem that the salt formed in the deactivation step of the used catalyst complicates the separation of itself.

As described hereinbefore, in spite of the various processes for production of a carboxylic acid ester which have been disclosed so far, none of them meets the industrial requirement at the present time. Nevertheless, the process for producing a carboxylic acid ester and formamide from a Carboxylic acid amide and Formic acid ester, etc. is industrially advantageous in many respects, and gives rise to the need for the development of a catalyst applicable to the process with excellent characteristics in many industrial aspects.

Under such circumstances intensive research and investigation were concentrated by the present inventors on the solution of the above various problems in the production of a carboxylic acid ester and formamide from a Carboxylic acid amide and Formic acid ester, etc.

As the result, it has been discovered by the present inventors that the use of a strongly basic anion-exchange resin as the catalyst in the aforesaid process enables the proceeding of the reaction under mild conditions and the production of the objective carboxylic acid ester with formamide with a high yield and high selectivity and further, greatly facilitates the separation, recovery and recycling of the catalyst. The present invention has been accomplished on the basis of the above-mentioned finding and information.

SUMMARY OF THE INVENTION

It is the object of the present invention to provide a process for producing a carboxylic acid ester and formamide with a high yield and high selectivity from a carboxylic acid amide and a formic acid ester or from a carboxylic acid amide, an alcohol and carbon monoxide.

For the above object, the present invention provides a process for producing a carboxylic acid ester and formamide which comprises reacting a carboxylic acid amide with a formic acid ester or with an alcohol and carbon monoxide in the presence of a strongly basic anion-exchange resin as the catalyst.

DESCRIPTION OF PREFERRED EMBODIMENT

The carboxylic acid amide to be employed in the process of the present invention is synthesized by the hydration reaction of a nitrile, reaction of an amine with carbon monoxide or the like and is exemplified by an aliphatic or aromatic carboxylic acid amide, α-hydroxycarboxylic acid amide and α-aminocarboxylic acid amide. Specific examples of carboxylic acid amides include acetamide, lactamide, acrylamide, methacrylamide, benzamide, α-hydroxyisobutyramide and alanine amide.

The alcohol and formic acid ester to be used in the process of the present invention are preferably an aliphatic alcohol having 1 to 10 carbon atoms and the ester of said alcohol and formic acid, respectively. Examples of such alcohol include methanol, ethanol, 1-propanol, 2-propanol, 1-butanol, 2-butanol and 1-pentanol. Examples of the above-mentioned formic acid ester include methyl formate, ethyl formate, isopropyl formate, n-butyl formate, sec-butyl formate and n-pentyl formate.

The strongly basic anion-exchange resin comprises a resin having a crosslinkage structure as the matrix and anion-exchange groups introduced therein. Examples of the resin as the matrix include styrene/divinylbenzene crosslinked polystyrene, polyacrylate derived from acrylic acid and heat-resisting aromatic polymer into which ether groups or carbonyl groups are introduced.

As the anion exchange group in ion exchange resin, amino group, substituted amino group and quaternary ammonium group are generally known. In the case of the strongly basic anion-exchange resin to be employed in the process of the present invention, the anion exchange group is a quaternary ammonium group into which trialkyl substituted-nitrogen atom $(N^+R_3)$ or dialkylethanolamine cation, e.g.—$N^+(CH_3)_2(C_2H_4OH)$ is introduced.

Such strongly basic anion-exchange resins are available in the market under the tradename, for example, Amberlist A-26, Dowex TG-550A, Lewatit M504, Diaion PA 306, etc.

When a carboxylic acid amide is reacted with a formic acid ester according to the process of the present invention, it is desirable to make use of a suitable solvent, since a carboxylic acid amide is generally in the form of solid at room temperature. The solvent is desirably a polar solvent such as an alcohol, particularly desirably an alcohol constituting the formic acid ester. When an alcohol and carbon monoxide are used in place of a formic acid ester as the starting material, it is preferable that the alcohol be used in an excess amount so that it can also function as the solvent for the carboxylic acid amide.

With regard to amount of the formic acid ester or alcohol to be used in the process of the present invention, the molar ratio of carboxylic acid amide to formic acid ester is 1:0.5 to 1:15, preferably 1:1 to 1:8. In the case of an alcohol and carbon monoxide being used in place of a formic acid ester, the molar ratio of carboxylic acid amide to alcohol is 1:1 to 1:30, preferably 1:2 to 1:20.

In addition, a carboxylic acid amide may be reacted with an alcohol and carbon monoxide in the presence of a formic acid ester as the case may be at a molar ratio of carboxylic acid amide/formic acid ester/alcohol of 1:0.5:0.5 to 1:15:30, preferably 1:1:2 to 1:8:15.

The above-mentioned molar ratio ranges are not specifically limited but may be appropriately selected taking into consideration the type of carboxylic amide, reaction conditions and the like.

On the other hand, the reaction temperature and reaction time in the process of the present invention can be selected from a wide range depending on the types of the starting material, the amount of the catalyst charged and the aimed conversion efficiency. The general reaction conditions include a reaction temperature in the range of 0° to 150° C., preferably 20° to 100° C. A reaction temperature lower than 0° C. results in failure to assure a practical reaction rate, whereas that exceeding 150° C. is disadvantageous since it is likely to bring about formamide decomposition and catalyst deactivation.

The reaction time is 0.1 to 20 hours, more generally 0.2 to 10 hours.

In regard to the pressure in the reaction of a carboxylic acid amide with a formic acid ester as starting materials in the process of the present invention, the reaction may be carried out under vapor pressures of the starting materials at the reaction temperature or under pressurized carbon monoxide for the purpose of preventing decomposition of the formic acid ester. In general, the reaction pressure is in the range of atmospheric pressure to 300 atm, preferably atmospheric pressure to 200 atm from the practical viewpoint in the reaction of a carboxylic acid amide with a formic acid ester.

In the case of the reaction of a carboxylic acid amide with an alcohol and carbon monoxide, the reaction pressure in terms of the partial pressure of carbon monoxide is in the range of 10 to 500 atm, preferably 30 to 400 atm from the practical standpoint.

The reaction system in the process of the present invention is not specifically limited but may be arbitrarily selected insofar as the starting materials are brought into contact with the strongly basic anion-exchange resin as the catalyst.

As the general reaction system, mention may be made of a fluidized bed, fixed bed, etc., and batchwise system, continuous system, etc.

In accordance with the process of the present invention hereinbefore described, it is possible to separate and recover the catalyst by a simplified operation from the liquid reaction product resulting from the reaction of a Carboxylic acid amide with a Formic acid ester, etc. and also to obtain with ease the carboxylic acid ester and formamide each having a high quality by applying distillation procedure to the liquid reaction product.

By virtue of the use of the strongly basic anion-exchange resin as the catalyst, the process according to the present invention enables the efficient production of the carboxylic acid ester as well as formamide from the Carboxylic acid amide and Formic acid ester, etc. with a high selectivity under mild reaction conditions and at the same time facilitates the separation of the catalyst from the resultant reaction product, thereby greatly enhancing the industrial significance of itself.

In the following, the present invention will be described in further detail with reference to examples, but it shall not be limited thereto.

EXAMPLE 1

In a 50 mL autoclave made of stainless steel was placed 10.3 g (0.1 mol) of α-hydroxyisobutyramide, which was then incorporated with 12.0 g (0.2 mol) of methyl formate and 9.6 g (0.3 mol) of methanol to dissolve the solid.

Then, to the mixture was added 1.0 g as the dry weight of the strongly basic anion-exchange resin (produced by Rohm & Haas Corp. under the tradename "Amberlist A-26") that had been previously treated with aqueous solution of 1N-NaOH into OH type to carry out reaction at 50° C. for 4 hours.

The content in the autoclave was cooled to 10° C., taken out therefrom and filtered to separate the catalyst from the liquid reaction product, which was then analyzed by gas chromatography.

As the result, the conversion of α-hydroxyisobutyramide was 58.2%, the selectivity to methyl α-hydroxyisobutyrate was 99.0% and the selectivity to formamide was 99.1% based on α-hydroxyisobutyramide.

EXAMPLE 2

The procedure in Example 1 was repeated except that 2.95 g (0.005 mol) of acetamide was used in place of α-hydroxyisobutyric amide.

As the result, the conversion of acetamide was 76.6%, the selectivity to methyl acetate was 98.8% and the selectivity to formamide was 97.0%.

EXAMPLE 3

The procedure in Example 1 was repeated except that 4.25 g (0.05 mol) of methacrylamide was used in place of α-hydroxyisobutyric amide.

As the result, the conversion of methacrylamide was 72.1%, the selectivity to methyl methacrylate was 94.2% and the selectivity to formamide was 96.7%.

EXAMPLE 4

The procedure in Example 1 was repeated except that 51 g (0.5 mol) of butyl formate and 22.2 g (0.3 mol) of butanol were used in place of methyl formate and methanol, respectively.

As the result, the conversion of α-hydroxyisobutyramide was 75.0%, the selectivity to butyl α-hydroxyisobutyrate was 93.9% and the selectivity to formamide was 92.0%.

EXAMPLE 5

The procedure in Example 1 was repeated except that Lewatit M504 (produced by Bayer AG) was used as the strongly basic anion-exchange resin in place of Amberlist A-26.

As the result, the conversion of α-hydroxyisobutyramide was 62.6%, the selectivity to methyl α-hydroxyisobutyrate was 99.6% and the selectivity to formamide was 98.8%.

EXAMPLE 6

In a 200 mL autoclave made of stainless steel were placed 10.3 g (0.1 mol) of α-hydroxyisobutyramide, 32 g (1.0 mol) of methanol and 1.0 g of the strongly basic anion-exchange resin, and the content was pressurized with carbon monoxide to 40 atm and thereafter shaked with heating. After the temperature in the autoclave reached 80° C., the reaction was continued for 3 hours while feeding carbon monoxide so as to maintain the reaction pressure at 40 atm.

The content in the autoclave was cooled to 10° C. and, after the inside pressure was gradually lowered to atmospheric pressure, taken out therefrom and analyzed in the same manner as in Example 1.

As the result, the conversion of α-hydroxyisobutyramide was 85.3%, the selectivity to methyl α-hydroxyisobutyrate was 98.1%, and the selectivity to formamide was 96.9%.

EXAMPLE 7

A tubular reactor made of stainless steel with 15 mm inside diameter and 300 mm length was packed with 50 ml of strongly basic anion-exchange resin (produced by Rohm & Haas Corp. under the tradename "Amberlite 900") as the catalyst, the layer of which was maintained at 50° C. by passing warm water through the jacket.

Subsequently, a mixed solution of α-hydroxyisobutyramide, methyl formate and methanol (molar ratio of 1:2:3) was fed to the catalyst layer at a flow rate of 16.6 g/hour. After 24 hours from the start of the reaction, the sample of liquid reaction product was collected for one hour and analyzed by gas chromatography.

As the result, the conversion of α-hydroxyisobutyramide was 63 3%, the selectivity to methyl α-hydroxyisobutyrate was 99.2% and the selectivity to formamide was 99.0% based on α-hydroxyisobutyramide.

The liquid reaction product obtained in this example in an amount of 200 g was distilled to produce 46.2 g of methyl α-hydroxyisobutyrate and 17.3 g of formamide at recovery rates of 99.2% and 97.6%, respectively.

COMPARATIVE EXAMPLE 1

The procedure in Example 7 was repeated except that the tubular reactor was packed with 50 mL of glass beads having 1 mm diameter in place of the strongly basic anion-exchange resin (Amberlite 900), and that 28% solution of $NaOCH_3$ in methanol was fed to the reaction tube at a flow rate of 0.5 g/hour along with the starting material.

As the result, the conversion of α-hydroxyisobutyramide was 64.2%, the selectivity to methyl α-hydroxyisobutyrate was 99.4% and the selectivity to formamide was 99.1% based on α-hydroxyisobutyramide. However, when the liquid reaction product thus obtained was distilled, a reverse reaction took place in the distillation still, causing methyl formate to be formed and distilled. Consequently, neither methyl α-hydroxyisobutyrate nor formamide could be isolated as the objective.

What is claimed is:

1. A process for producing a carboxylic acid ester and formamide which comprises reacting a carboxylic acid amide with a formic acid ester or reacting a carboxylic acid amide with an alcohol and carbon monoxide, in the presence of a strongly basic anion-exchange resin at a temperature of 0° C. to 150° C.

2. The process according to claim 1 wherein a carboxylic acid amide is reacted with a formic acid ester.

3. The process according to claim 1 wherein a carboxylic acid amide is reacted with an alcohol and carbon monoxide in the absence or presence of a formic acid ester.

4. The process according to claim 1 wherein said anion-exchange resin has anion-exchange groups comprising quaternary ammonium groups having trialkyl-substituted nitrogen atoms.

5. The process according to claim 1 wherein said anion-exchange resin has anion-exchange groups comprising quaternary ammonium groups having dialkylethanolamine cations.

6. The process according to claim 1 wherein said carboxylic acid amide is an aliphatic carboxylic acid amide.

7. The process according to claim 1 wherein said carboxylic acid amide is an α-hydroxycarboxylic acid amide.

8. The process according to claim 1 wherein said carboxylic acid amide is that produced by hydration reaction of a nitrile or synthesis of an amine and carbon monoxide.

9. The process according to claim 1 wherein said alcohol is an aliphatic alcohol having 1 to 10 carbon atoms.

10. The process according to claim 1 wherein said formic acid ester is an ester of an aliphatic alcohol having 1 to 10 carbon atoms with formic acid.

11. The process according to claim 2 wherein the carboxylic acid amide is selected from the group consisting of acetamide, lactamide, acrylamide, methacrylamide, benzamide, α-hydroxyisobutyramide and alanine amide; the formic acid ester is selected from the group consisting of methyl formate, ethyl formate, isopropyl formate, n-butyl formate, sec-butyl formate and n-pentyl formate; and the molar ratio of the carboxylic acid amide to the formic acid ester is 1:0.5 to 1:15.

12. The process according to claim 11 wherein the molar ratio of the carboxylic acid amide to the formic acid ester is 1:1 to 1:8; the temperature is 20° to 100° C. and the process is carried out for a reaction time of 0.1 to 20 hours and at a pressure of atmospheric pressure to 300 atm.

13. The process according to claim 12 wherein the strongly basic anion-exchange resin comprises a resin having a crosslinkage structure as a matrix with an anion-exchange group disposed therein, wherein said matrix is selected from the group consisting of styrene/divinylbenzene crosslinked polystyrene and polyacrylate derived from acrylic acid heat-resistant aromatic polymer into which ether groups and carbonyl group are introduced.

14. The process according to claim 13 wherein the anion exchange group is selected from the group consisting of a trialkyl substituted-nitrogen atom and a dialkylethanolamine group.

15. The process according to claim 3 wherein the alcohol is selected from the group consisting of methanol, ethanol, 1-propanol, 2-propanol, 1-butanol, 2-butanol and 1-pentanol; and the molar ratio of the carboxylic acid amide to the alcohol is 1:1 to 1:30.

16. The process according to claim 15 wherein the molar ratio of the carboxylic acid amide to the alcohol is 1:2 to 1:20; the temperature is 20° to 100° C. and the process is carried out for a reaction time of 0.1 to 20 hours, and at a carbon monoxide partial pressure of 10 to 500 atm.

17. The process according to claim 16 wherein the strongly basic anion-exchange resin comprises a resin having a crosslinkage structure as a matrix with an anion-exchange group disposed therein, wherein said matrix is selected from the group consisting of styrene/divinylbenzene crosslinked polystyrene and polyacrylate derived from acrylic acid heat-resistant aromatic polymer into which ether groups and carbonyl groups are introduced.

18. The process according to claim 17 wherein the anion exchange group is selected from the group consisting of a trialkyl substituted-nitrogen atom and a dialkylethanolamine group.

19. The process according to claim 3 which is carried out in the presence of a formic acid ester, wherein the molar ratio of carboxylic acid amide/formic acid ester/alcohol is 1:0.5:0.5 to 1:15:30; the carboxylic acid amide is selected from the group consisting of acetamide, lactamide, acrylamide, methacrylamide, benzamide, α-hydroxyisobutyramide and alanine amide; the alcohol is selected from the group consisting of methanol, ethanol, 1-propanol, 2-propanol, 1-butanol, 2-butanol and 1-pentanol; and the formic acid ester is selected from the group consisting of methyl formate, ethyl formate, isopropyl formate, n-butyl formate, sec-butyl formate and n-pentyl formate.

20. The process according to claim 19 wherein the molar ratio of carboxylic acid amide/formic acid ester/alcohol is 1:1:2 to 1:8:15; the temperature is 20° to 100° C. and the process is carried out at a pressure time of 0.1 to 20 hours, and a carbon monoxide partial pressure of 10 to 50 atm.

* * * * *